(12) United States Patent
Bolan et al.

(10) Patent No.: US 7,702,378 B2
(45) Date of Patent: Apr. 20, 2010

(54) TISSUE MARKER FOR MULTIMODALITY RADIOGRAPHIC IMAGING

(75) Inventors: Patrick J. Bolan, Minneapolis, MN (US); Michael Garwood, Medina, MN (US); Michael T. Nelson, Golden Valley, MN (US); Daniel A. Halpern, St. Louis Park, MN (US)

(73) Assignee: Breast-Med, Inc., Golden Valley, MN (US)

( * ) Notice: Subject to any disclaimer, the term of this patent is extended or adjusted under 35 U.S.C. 154(b) by 658 days.

(21) Appl. No.: 11/281,801

(22) Filed: Nov. 17, 2005

(65) Prior Publication Data

US 2007/0110665 A1    May 17, 2007

(51) Int. Cl.
*A61B 5/05* (2006.01)

(52) U.S. Cl. ................ 600/414; 600/420; 600/424; 600/426

(58) Field of Classification Search ............ 600/414, 600/420, 424, 426, 431
See application file for complete search history.

(56) References Cited

U.S. PATENT DOCUMENTS

| | | | |
|---|---|---|---|
| 5,016,639 A | 5/1991 | Allen | |
| 5,097,839 A | 3/1992 | Allen | |
| 5,119,817 A | 6/1992 | Allen | |
| 5,179,955 A | 1/1993 | Leveen et al. | |
| 5,211,164 A | 5/1993 | Allen | |
| 5,394,457 A | 2/1995 | Leibinger et al. | |
| 5,397,329 A | 3/1995 | Allen | |
| 5,405,402 A | 4/1995 | Dye et al. | |
| 5,469,847 A * | 11/1995 | Zinreich et al. | ............ 600/414 |
| 5,609,850 A | 3/1997 | Deutsch et al. | |
| 5,702,128 A | 12/1997 | Maxim et al. | |
| 5,769,861 A | 6/1998 | Vilsmeier | |
| 5,782,764 A * | 7/1998 | Werne | ............ 600/411 |
| 6,128,522 A | 10/2000 | Acker et al. | |
| 6,161,034 A | 12/2000 | Burbank et al. | |
| 6,181,960 B1 | 1/2001 | Jenson et al. | |
| 6,269,148 B1 | 7/2001 | Jessop et al. | |
| 6,270,464 B1 | 8/2001 | Fulton, III et al. | |

(Continued)

FOREIGN PATENT DOCUMENTS

CA    2579914 A1    11/2006

(Continued)

OTHER PUBLICATIONS

Bolan, P. J., et al., "A Novel Soft Tissue Marker for Multimodal Breast Imagine with Positive MRI Contrast", *Joint Annual Meeting ISMRM-ESMRMB*, (May 2007), 1 pg.

(Continued)

*Primary Examiner*—Brian Casler
*Assistant Examiner*—Peter Luong
(74) *Attorney, Agent, or Firm*—Schwegman Lundberg & Woessner, P.A.

(57) ABSTRACT

An implantable tissue marker incorporates a contrast agent sealed within a chamber in a container formed from a solid material. The contrast agent is selected to produce a change, such as an increase, in signal intensity under magnetic resonance imaging (MRI). An additional contrast agent may also be sealed within the chamber to provide visibility under another imaging modality, such as computed tomographic (CT) imaging or ultrasound imaging.

62 Claims, 5 Drawing Sheets

U.S. PATENT DOCUMENTS

| | | | |
|---|---|---|---|
| 6,333,971 B2 * | 12/2001 | McCrory et al. ............ 378/162 |
| 6,347,241 B2 | 2/2002 | Burbank et al. |
| 6,350,244 B1 | 2/2002 | Fisher |
| 6,356,782 B1 | 3/2002 | Sirimanne et al. |
| 6,371,904 B1 | 4/2002 | Sirimanne et al. |
| 6,374,132 B1 | 4/2002 | Acker et al. |
| 6,394,965 B1 | 5/2002 | Klein |
| 6,405,072 B1 | 6/2002 | Cosman |
| 6,419,680 B1 * | 7/2002 | Cosman et al. ............ 606/130 |
| 6,427,081 B1 | 7/2002 | Burbank et al. |
| 6,487,438 B1 | 11/2002 | Widmark et al. |
| 6,516,211 B1 | 2/2003 | Acker et al. |
| 6,544,185 B2 | 4/2003 | Montegrande |
| 6,546,279 B1 | 4/2003 | Bova et al. |
| 6,549,802 B2 | 4/2003 | Thorton |
| 6,567,689 B2 | 5/2003 | Burbank et al. |
| 6,575,991 B1 | 6/2003 | Chesbrough et al. |
| 6,605,047 B2 | 8/2003 | Zarins et al. |
| 6,632,176 B2 | 10/2003 | McIntire et al. |
| 6,635,064 B2 | 10/2003 | U et al. |
| 6,656,192 B2 | 12/2003 | Espositio et al. |
| 6,662,041 B2 | 12/2003 | Burbank et al. |
| 6,699,205 B2 | 3/2004 | Fulton, III et al. |
| 6,725,083 B1 | 4/2004 | Burbank et al. |
| 6,730,042 B2 | 5/2004 | Fulton et al. |
| 6,746,661 B2 | 6/2004 | Kaplan |
| 6,761,679 B2 | 7/2004 | Sajo et al. |
| 6,773,408 B1 | 8/2004 | Acker et al. |
| 6,778,850 B1 | 8/2004 | Adler et al. |
| 6,862,470 B2 | 3/2005 | Burbank et al. |
| 6,927,406 B2 | 8/2005 | Zyromski |
| 6,993,375 B2 | 1/2006 | Burbank et al. |
| 6,996,433 B2 | 2/2006 | Burbank et al. |
| 7,010,340 B2 | 3/2006 | Scarantino et al. |
| 7,044,957 B2 | 5/2006 | Foerster et al. |
| 7,047,063 B2 | 5/2006 | Burbank et al. |
| 2002/0035324 A1 | 3/2002 | Sirimanne et al. |
| 2002/0083951 A1 | 7/2002 | Stegmaier et al. |
| 2002/0107437 A1 | 8/2002 | Sirimanne et al. |
| 2002/0161298 A1 | 10/2002 | Burbank et al. |
| 2002/0188196 A1 | 12/2002 | Burbank et al. |
| 2004/0030262 A1 | 2/2004 | Fisher et al. |
| 2004/0193044 A1 | 9/2004 | Burbank et al. |
| 2004/0236211 A1 | 11/2004 | Burbank et al. |
| 2004/0236212 A1 | 11/2004 | Jones et al. |
| 2004/0236213 A1 | 11/2004 | Jones et al. |
| 2005/0004456 A1 | 1/2005 | Thomas et al. |
| 2005/0020916 A1 | 1/2005 | MacFarlane et al. |
| 2005/0033157 A1 | 2/2005 | Klein et al. |
| 2005/0059884 A1 | 3/2005 | Kragg |
| 2005/0065393 A1 | 3/2005 | Miller |
| 2005/0143656 A1 | 6/2005 | Burbank et al. |
| 2005/0205445 A1 | 9/2005 | Seilet et al. |
| 2005/0234336 A1 | 10/2005 | Beckman et al. |
| 2005/0255045 A1 | 11/2005 | Woltering |
| 2006/0036165 A1 | 2/2006 | Burbank et al. |
| 2006/0058645 A1 | 3/2006 | Komistek et al. |
| 2006/0058648 A1 | 3/2006 | Meier et al. |
| 2006/0084865 A1 | 4/2006 | Burbank et al. |
| 2006/0122503 A1 | 6/2006 | Burbank et al. |
| 2006/0155190 A1 | 7/2006 | Brubank et al. |
| 2006/0293581 A1 | 12/2006 | Plewes et al. |
| 2007/0087026 A1 | 4/2007 | Filed |
| 2007/0118034 A1 | 5/2007 | Mark |
| 2007/0142725 A1 | 6/2007 | Hardin et al. |
| 2008/0033286 A1 | 2/2008 | Whitmore et al. |
| 2008/0234572 A1 | 9/2008 | Jones |
| 2009/0105584 A1 | 4/2009 | Jones |

FOREIGN PATENT DOCUMENTS

| | | |
|---|---|---|
| EP | 1491147 A1 | 12/2004 |
| EP | 1579878 A1 | 9/2005 |
| WO | WO-9717103 A1 | 5/1997 |
| WO | WO-0024332 A1 | 5/2000 |
| WO | WO-0038579 A2 | 7/2000 |
| WO | WO-0230482 A1 | 4/2002 |
| WO | WO-03022133 A2 | 3/2003 |
| WO | WO-03051452 A1 | 6/2003 |
| WO | WO-2004084738 A1 | 10/2004 |
| WO | WO-2005046733 A1 | 5/2005 |
| WO | WO-2005063126 A2 | 7/2005 |
| WO | WO-2006119645 A1 | 11/2006 |
| WO | WO-2007060576 A2 | 5/2007 |

OTHER PUBLICATIONS

Frank, Steven J., et al., "A Novel MRI Marker for Prostate Brachytherapy", *Int. J. Radiation Oncology Biol. Phys.*, vol. 70, No. 1, (2008), 5-8.

Ellis, R. E., et al., "Use of Biocompatible Fiducial Marker in Evaluating the Accuracy of CT Image Registration", *Investigative Radiology*, (1996), 1-9.

Gierga, D. P., et al., "The Correlation between Internal and External Markers for Abdominal Tumors: Implications for Respiratory Gating", *Int J Radiat Oncol Biol Phys.*; 61(f); 1551-8, (Apr. 1, 2005), 1 page.

Igdem, S., et al., "Implantation of Fiducial Markers for Image Guidance in Prostate Radiotherapy: Patient-reported toxicity", *The British Journal of Radiology*, (2009), 1-5.

Maier-Hein, L, et al., "On Combining Internal and External Fiducials for Liver Motion Compensation", *Comput Aided Surg.*; 13(6): 369-76, (Nov. 2008), 1 page.

* cited by examiner

TISSUE MARKER FOR MULTIMODALITY RADIOGRAPHIC IMAGING

TECHNICAL BACKGROUND

The disclosure relates generally to tissue markers. More particularly, the disclosure relates to implantable tissue markers for use in magnetic resonance imaging.

BACKGROUND

Certain medical conditions, including breast cancer, are increasingly being diagnosed and treated using minimally invasive medical techniques. Such techniques typically involve the use of clinical imaging methods that allow the physician to visualize interior portions of a patient's body without the need to make excessive incisions. Imaging can be performed using any of variety of modalities, including, for example, X-rays, computed tomographic (CT) X-ray imaging, portal film imaging devices, electronic portal imaging devices, electrical impedance tomography (EIT), magnetic resonance (MR) imaging, or MRI, magnetic source imaging (MSI), magnetic resonance spectroscopy (MRS), magnetic resonance mammography (MRM), magnetic resonance angiography (MRA), magnetoelectro-encephalography (MEG), laser optical imaging, electric potential tomography (EPT), brain electrical activity mapping (BEAM), arterial contrast injection angiography, and digital subtraction angiography. Nuclear medicine modalities include positron emission tomography (PET) and single photon emission computed tomography (SPECT).

Some of these imaging procedures involve the use of radiographic markers. Radiographic markers are small devices that are implanted in a patient during surgical procedures, such as biopsies. Conventional markers typically consist of one or more solid objects, such as a piece of metallic wire, ceramic beads, etc., which are implanted either by themselves or within a gelatinous matrix to temporarily increase visibility, for example, to ultrasound imaging. They are designed to be visible to one of the imaging modalities listed above and typically have a shape that is readily identifiable as an artificial structure, as contrasted from naturally occurring anatomical structures in the patient's body. For example, markers can be shaped as coils, stars, rectangles, spheres, or other shapes that do not occur in anatomical structures. Such markers enable radiologists to localize the site of surgery in subsequent imaging studies or to facilitate image registration during image-guided therapeutic procedures. In this way, markers can serve as landmarks that provide a frame of reference for the radiologist.

Most conventional markers appear as a signal void, i.e., a dark artifact, in magnetic resonance imaging. This manifestation can be particularly problematic in some contexts. For example, heterogeneous breast tissue produces many dark artifacts under MR imaging, thereby rendering small signal voids produced by some conventional markers difficult to identify and distinguish from naturally occurring dark artifacts. In addition, some markers produce large susceptibility artifacts under MR imaging, thereby distorting images in both MRI and spectroscopic modalities. Some markers incorporate an external gel that may produce a positive or bright signal, but such gels are not permanent. Some other markers contain collagen or polylactic acid, which may interfere with magnetic resonance spectroscopy. With the increasing use of MR imaging techniques in the treatment of breast cancer in clinical settings, improved MR visibility of tissue markers is particularly desirable.

SUMMARY OF THE DISCLOSURE

According to various example embodiments, an implantable tissue marker incorporates a contrast agent sealed within a chamber in a container formed from a solid material. The contrast agent is selected to produce a change in signal intensity under magnetic resonance imaging (MRI). An additional contrast agent may also be sealed within the chamber to provide visibility under another imaging modality, such as computed tomographic (CT) imaging or ultrasound imaging.

One embodiment is directed to a permanently implantable radiographic marker. A container formed from a solid material defines an internal chamber, in which a contrast agent is sealed. The contrast agent is selected to produce an increase in signal intensity in a magnetic resonance (MR) imaging modality. Another embodiment is directed to a method of manufacturing such a marker.

In another embodiment, a permanently implantable fiducial marker includes a container formed from a nonbiodegradable solid material. The container defines an internal chamber. A first contrast agent is sealed within the internal chamber and is selected to produce an increase in signal intensity in a magnetic resonance (MR) imaging modality. A second contrast agent sealed within the internal chamber. The second contrast agent is selected to produce a signal in another imaging modality.

Another embodiment is directed to a method of identifying a location within a body of a patient. A marker is implanted proximate the location. The marker comprises a container formed from a solid material and defining an internal chamber, and a contrast agent sealed within the internal chamber. The contrast agent is selected to produce an increase in signal intensity in a magnetic resonance (MR) imaging modality. A first image of the location is generated in the magnetic resonance (MR) imaging modality.

Various embodiments may provide certain advantages. For instance, a contrast agent selected to produce an increase in signal intensity in an MR imaging modality may produce good visualization characteristics without also producing an excessive artifact and without interfering with MR spectroscopy. Production of an increase in signal intensity in an MR imaging modality may be particularly beneficial in certain contexts, such as, for example, imaging of breast tissue, which is heterogeneous.

Additional objects, advantages, and features will become apparent from the following description and the claims that follow, considered in conjunction with the accompanying drawings.

DESCRIPTION OF VARIOUS EMBODIMENTS

According to various embodiments, an implantable tissue marker incorporates a contrast agent sealed within a chamber in a container formed from a solid material. The contrast agent is selected to produce an increase in signal intensity under magnetic resonance imaging (MRI). An additional contrast agent may also be sealed within the chamber to provide visibility under another imaging modality, such as computed tomographic (CT) imaging or ultrasound imaging.

In this way, certain advantages may be realized. For instance, a contrast agent selected to produce an increase in signal intensity in an MR imaging modality may produce good visualization characteristics without also producing an excessive artifact and without interfering with MR spectroscopy. Producing an increase in signal intensity in an MR imaging modality may be particularly beneficial in certain contexts, such as, for example, imaging of breast tissue. Most conventional markers appear as a signal void in MR imaging. The heterogeneous nature of breast tissue makes small signal voids difficult to identify. By producing an increase in signal intensity, i.e., a bright area, in MR imaging, the implantable tissue markers disclosed herein may be easier to see than conventional markers.

The following description of various embodiments implemented in the context of imaging certain types of tissue is to be construed by way of illustration rather than limitation. This description is not intended to limit the invention or its applications or uses. For example, while various embodiments are described as being implemented in the context of imaging breast tissue, it will be appreciated that the principles of the disclosure are applicable to other contexts, such as image registration during image guided therapeutic procedures.

In the following description, numerous specific details are set forth in order to provide a thorough understanding of various embodiments. It will be apparent to one skilled in the art that some embodiments may be practiced without some or all of these specific details. In other instances, well known components and process steps have not been described in detail.

Figure 1:
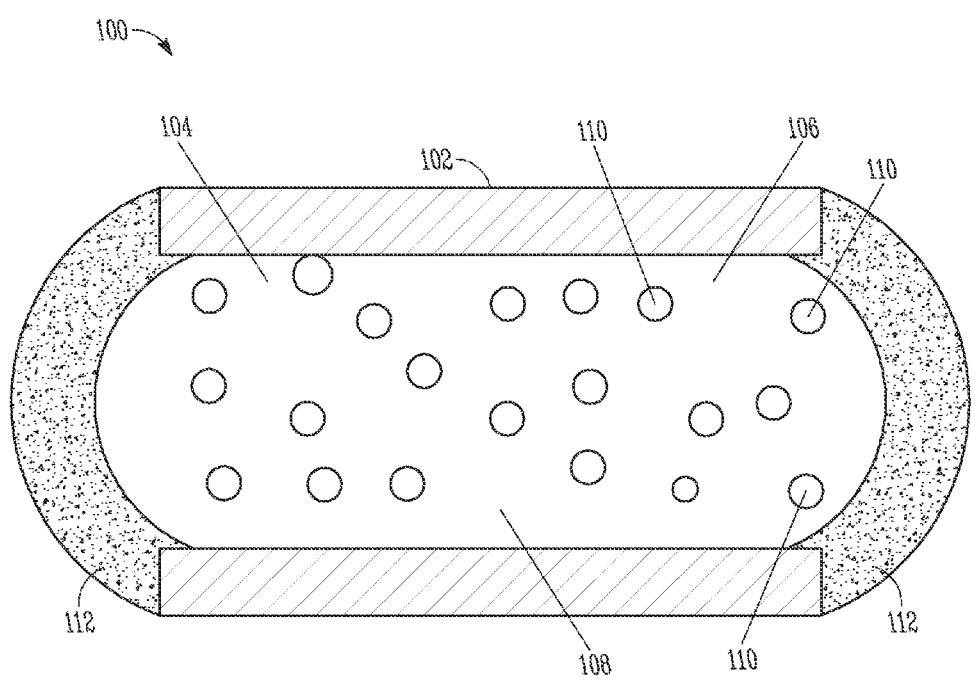
FIG. 1 is a sectional view of a tissue marker according to one embodiment.

Referring now to the drawings, FIG. 1 is a sectional view illustrating an example implantable radiographic marker 100 according to one embodiment. A tube 102 is formed from a nonbiodegradable radiopaque solid material, such as glass, plastic, carbon fiber, or silicone. For example, the tube 102 may be formed from LEXAN® polycarbonate resin, commercially available from General Electric Company, headquartered in Pittsfield, Mass. The tube 102 is preferably sized for insertion via a biopsy cannula. For example, in one particular implementation, the tube 102 has a major dimension of approximately 3-4 mm and a minor dimension of approximately 1-2 mm.

The tube 102 defines two end portions 104 and 106, at least one of which is initially open. A chamber 108 is defined within the tube 102 between the two end portions 104 and 106. One or more contrast agents 110 are introduced into the chamber 108. The end portions 104 and 106 are then sealed, for example, using a sealant 112 such as epoxy. In some embodiments, a permanent biocompatible adhesive such as cyanoacrylate serves as the sealant 112.

The visual representation of the contrast agents 110 in FIG. 1 is intended only to distinguish the contrast agents 110 from the chamber 108 in which they are disposed. According to various embodiments, the contrast agents 110 can be implemented as a gas, gel, or liquid, or as a combination of gases, gels, and/or liquids. Each of these materials can be selected independently to customize the appearance of the marker 100 in different imaging modalities and under different conditions, e.g., with or without contrast, and in various tissue types.

For instance, if the marker 100 is to be visible in magnetic resonance (MR) and computed tomographic (CT) imaging modalities, the chamber 108 may contain a mixture of a gadolinium-DTPA MR contrast agent and an iodinated CT contrast agent. The volume of contrast agent 110 in the chamber 108 may be maximized to promote visibility. Visibility is also promoted by matching the magnetic susceptibility of the contrast agent 110 and the magnetic susceptibility of the tube 102. If it is further desired that the marker 100 be visible in an ultrasound imaging modality, the chamber 108 may also contain an air bubble.

In some embodiments, the tube 102 itself, rather than multiple contrast agents 110, may provide visibility in certain imaging modalities. For example, the tube 102 may be made of a radiopaque polymer that provides contrast in X-ray imaging modalities. As another example, a difference in acoustic impedance between the tube 102 and the material in the chamber 108 will cause the marker 100 to reflect ultrasound waves, thereby promoting visibility in an ultrasound imaging modality. Further, if the magnetic susceptibility of the tube 102 is similar to that of the material in the chamber 108 and to that of the surrounding tissue, visibility in MR imaging modalities will be improved due to reduction of $T_2$ darkening.

In one particular embodiment, the marker 100 is formed by cutting a glass micropipette, commercially available from Fisher Scientific, headquartered in Hampton, N.H., to the desired length, e.g., 4 mm, to form the tube 102. The micropipette has an outer diameter appropriate for insertion via a biopsy cannula, e.g., 2 mm.

Contrast agents 110 are then introduced into the chamber 108 defined by the tube 102. In one particular embodiment, for example, an MR contrast agent and a CT contrast agent are combined, and the liquid mixture resulting from this combination is injected into the micropipette via a syringe of appropriate gauge, e.g., 25 ga. The MR contrast agent may be implemented as a gadolinium-based MR contrast agent, such as MAGNEVIST® MR contrast agent, commercially available from Berlex, headquartered in Montville, N.J. Other MR contrast agents include, but are not limited to, OMNISCAN™ MR contrast agent, commercially available from GE Healthcare, headquartered in Chalfont St. Giles, United Kingdom, PROHANCE® MR contrast agent, and OPTIMARK® MR contrast agent, commercially available from Tyco Healthcare/Mallinckrodt, Inc., headquartered in St. Louis, Mo. The CT contrast agent may be implemented as an iodinated CT contrast agent, such as OMNIPAQUE™ CT contrast agent, commercially available from GE Healthcare, headquartered in Chalfont St. Giles, United Kingdom. Other CT contrast agents include, but are not limited to, HEXABRIX®, TELEBRIX®, and CONRAY® CT contrast agents, commercially available from Tyco Healthcare/Mallinckrodt, Inc., headquartered in St. Louis, Mo. After the mixture is injected in the chamber 108, the ends of the tube 102 are sealed using a quick-setting epoxy.

Markers 100 of the type illustrated in FIG. 1 and described above have been evaluated for visibility in multiple imaging modalities. Markers 100 were made according to the above-described procedure and were suspended in a gelatin phantom. Magnetic resonance imaging (MRI) was performed on the gelatin phantom using a Siemens Trio 3T (3 Tesla) human MRI scanner. The MRI process used $T_1$-weighted 3D fast low angle shot (FLASH) images, which are typical for MR examinations of breast tissue. In addition, the gelatin phantom was also imaged using a clinical breast X-ray mammography system and a breast ultrasound using standard settings.

Figure 4:
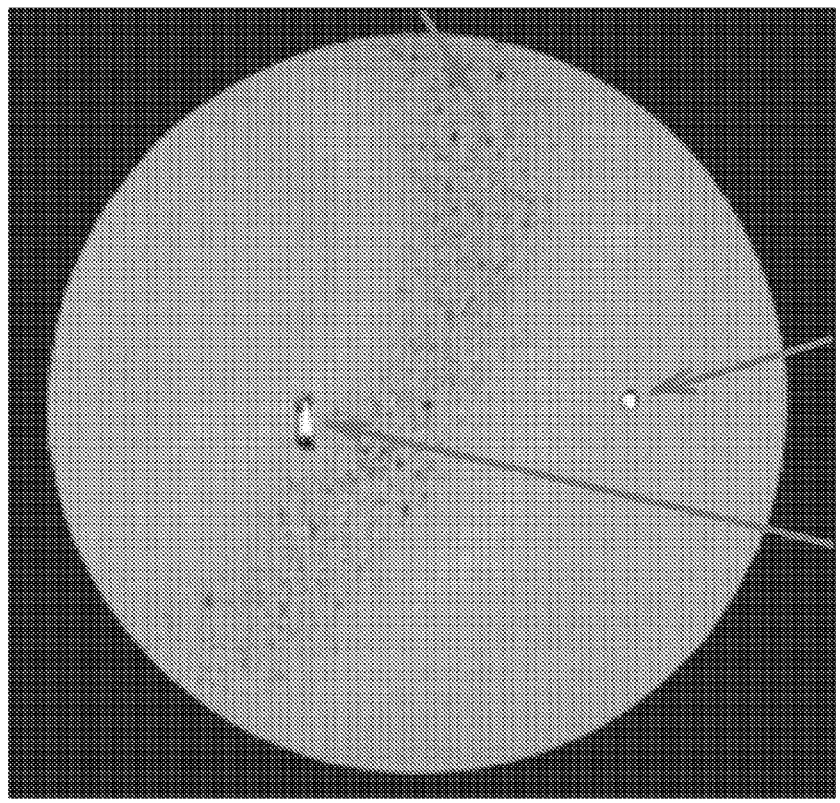
FIG. 4 is an image of the tissue marker of FIG. 1 as visible in a magnetic resonance imaging (MRI) modality.
Figure 5:
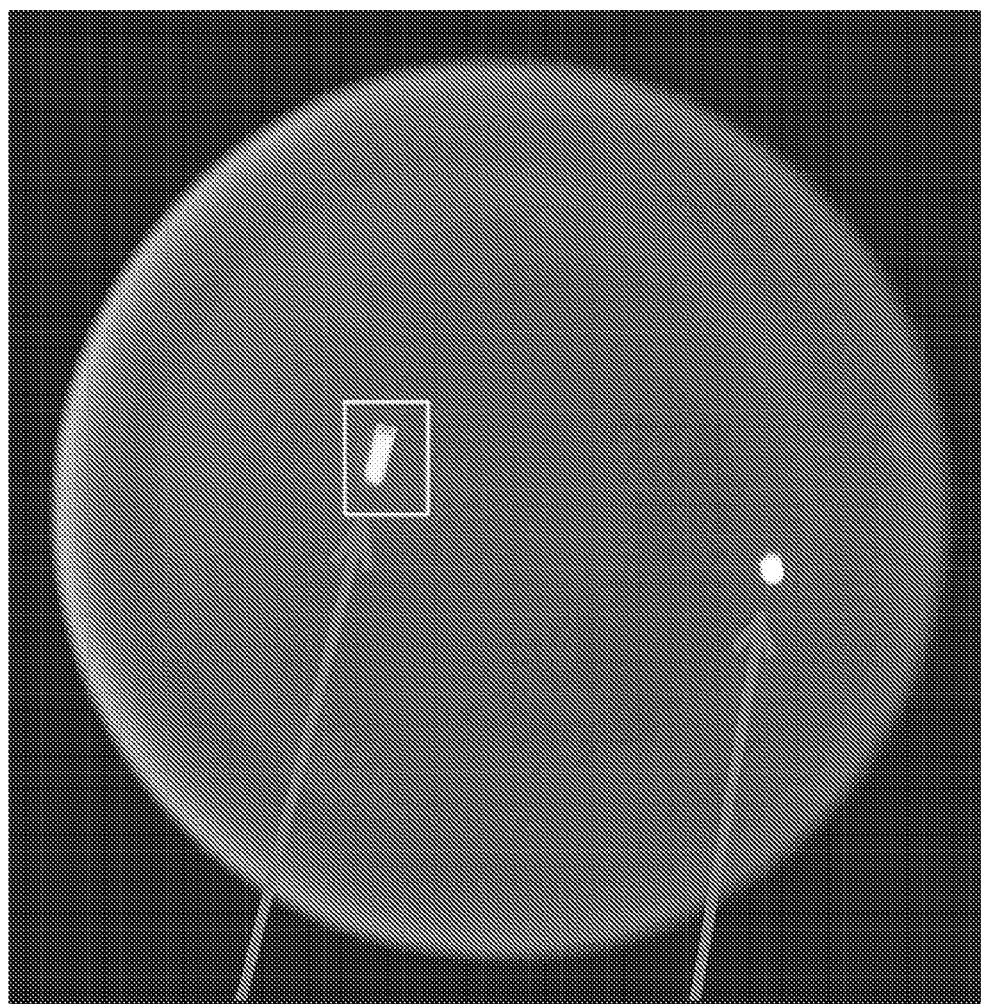
FIG. 5 is an image of the tissue marker of FIG. 1 as visible in a mammography modality.
Figure 6:
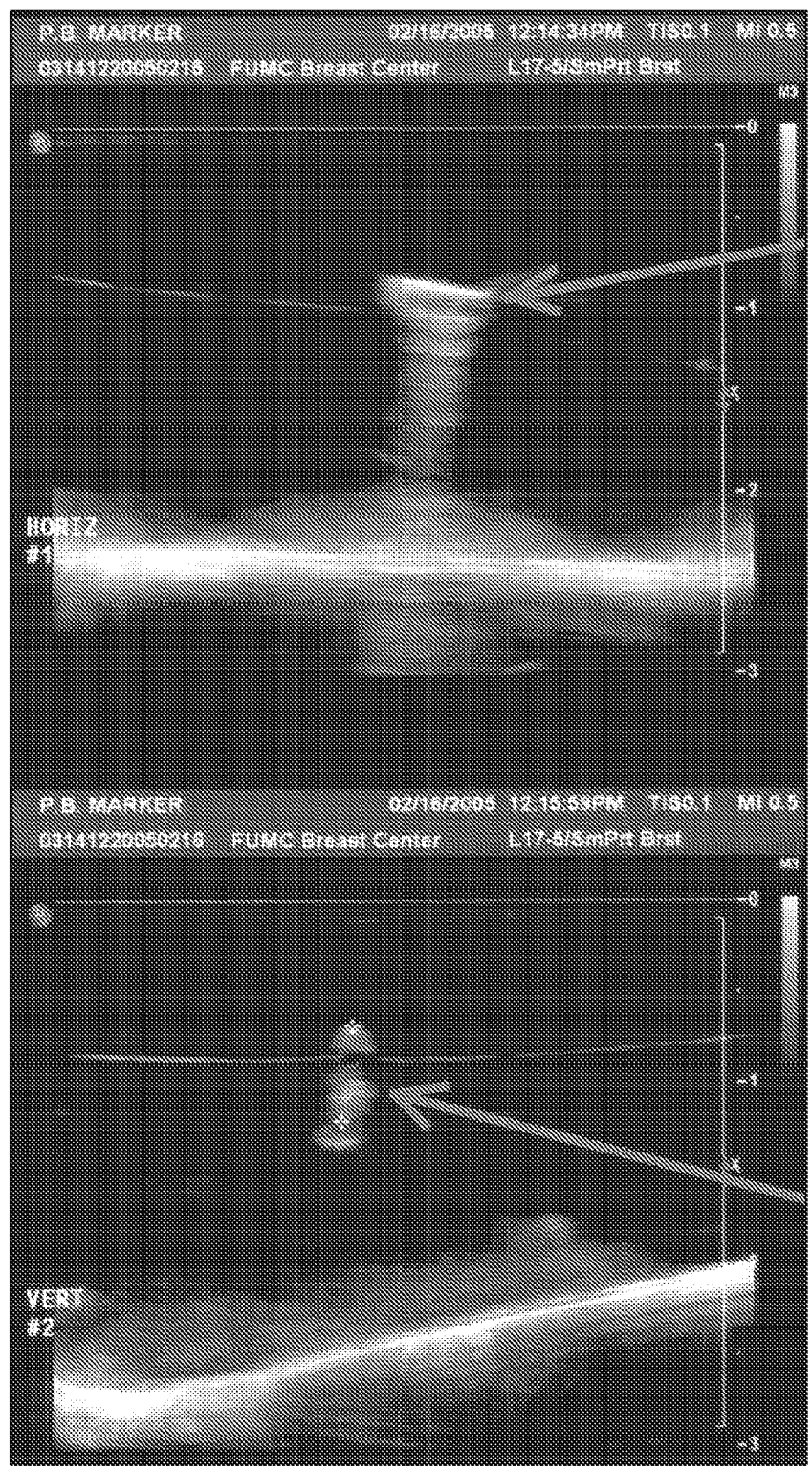
FIG. 6 is an image of the tissue marker of FIG. 1 as visible in an ultrasound imaging modality.

The evaluation of the markers 100 demonstrated that the markers 100 were clearly visible on the three modalities, namely, MRI, X-ray mammography, and ultrasound. FIGS. 4-6 are images of markers 100 obtained under the MRI, X-ray mammography, and ultrasound modalities, respectively. The markers 100 appeared as small signal voids, i.e., dark spots, under low-resolution MRI (0.8 mm in plane). However, the contrast agent 110 in the chamber 108 appeared hyperintense, that is, as bright spots, under higher MRI resolutions, e.g., 0.4 mm in plane. Accordingly, using higher MRI resolutions, the markers 100 are more clearly distinguishable from surrounding tissue than conventional markers that appear as signal voids. The bright signal seen at higher MRI resolutions may be particularly advantageous in imaging heterogeneous breast tissue, in which signal voids may be difficult to see.

In addition to the MRI modality, the markers 100 were also visible in the X-ray mammography and ultrasound imaging modalities. In the X-ray mammography modality, the radiopaque liquid occupying the chamber 108 could be seen clearly with distinct edges. In the ultrasound modality, the tube 102 appeared hyperechoic, while the contrast agents 110 occupying the chamber 108 appeared dark. In this modality, the markers 100 were most easily seen when they were oriented parallel to the transducer surface. However, the markers 100 could also be detected when they were oriented perpendicular to the transducer surface.

According to various embodiments, the contrast agents 110 that are sealed within the chamber 108 can be selected for visibility in any of a number of imaging modalities. Besides the MR, X-ray, and ultrasound imaging modalities mentioned above, contrast agents can be selected for visibility in computed tomographic (CT) X-ray imaging, fluoroscopy, portal film imaging, electronic portal imaging, electrical impedance tomography (EIT), magnetic source imaging (MSI), magnetic resonance spectroscopy (MRS), magnetic resonance mammography (MRM), magnetic resonance angiography (MRA), magnetoelectro-encephalography (MEG), laser optical imaging, electric potential tomography (EPT), brain electrical activity mapping (BEAM), arterial contrast injection angiography, and digital subtraction angiography modalities. Nuclear medicine modalities include positron emission tomography (PET) and single photon emission computed tomography (SPECT). In addition, as additional imaging modalities are developed in the future, it will be possible to seal contrast agents within the chamber 108 that are selected for visibility in such future modalities.

Figure 2:
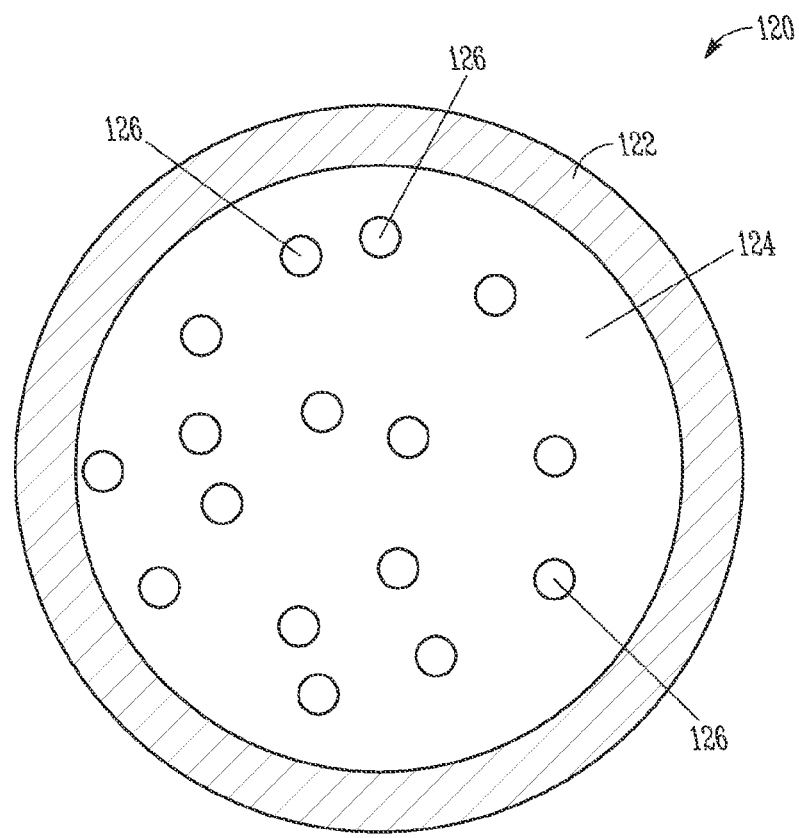
FIG. 2 is a sectional view of a tissue marker according to another embodiment.

FIG. 2 is a sectional view of another example tissue marker 120 according to another embodiment. The tissue marker 120 incorporates an outer capsule 122 formed from a nonbiodegradable radiopaque solid material, such as silicone. The capsule 122 is generally spherical in shape and is preferably sized for insertion via a biopsy cannula. The capsule 122 defines an internal chamber 124.

One or more contrast agents 126 are introduced into the chamber 124, for example, by injecting the contrast agents 126 into the chamber 124. The visual representation of the contrast agents 126 in FIG. 2 is intended only to distinguish the contrast agents 126 from the chamber 124 in which they are disposed. According to various embodiments, the contrast agents 126 can be implemented as a gas, gel, or liquid, or as a combination of gases, gels, and/or liquids. Each of these materials can be selected independently to customize the appearance of the marker 120 in different imaging modalities and under different conditions, e.g., with or without contrast, and in various tissue types. For instance, if the marker 120 is to be visible in magnetic resonance (MR) and computed tomographic (CT) imaging modalities, the chamber 124 may contain a mixture of a gadolinium-DTPA MR contrast agent, such as MAGNEVIST® MR contrast agent, and an iodinated CT contrast agent, such as OMNIPAQUE™ CT contrast agent. The volume of contrast agent 126 in the chamber 124 may be maximized to promote visibility. Visibility is also promoted by matching the magnetic susceptibility of the contrast agent 126 and the magnetic susceptibility of the capsule 122. If it is further desired that the marker 120 be visible in an ultrasound imaging modality, the chamber 124 may also contain an air bubble. After the mixture is injected in the chamber 124, the capsule 122 is sealed.

In some embodiments, the capsule 132 itself, rather than multiple contrast agents 136, may provide visibility in certain imaging modalities. For example, the capsule 132 may be made of a radiopaque polymer that provides contrast in X-ray imaging modalities. As another example, a difference in acoustic impedance between the capsule 132 and the material in the chamber 134 will cause the marker 130 to reflect ultrasound waves, thereby promoting visibility in an ultrasound imaging modality. Further, if the magnetic susceptibility of the capsule 132 is similar to that of the material in the chamber 134 and to that of the surrounding tissue, visibility in MR imaging modalities will be improved due to reduction of $T_2$ darkening.

Figure 3:
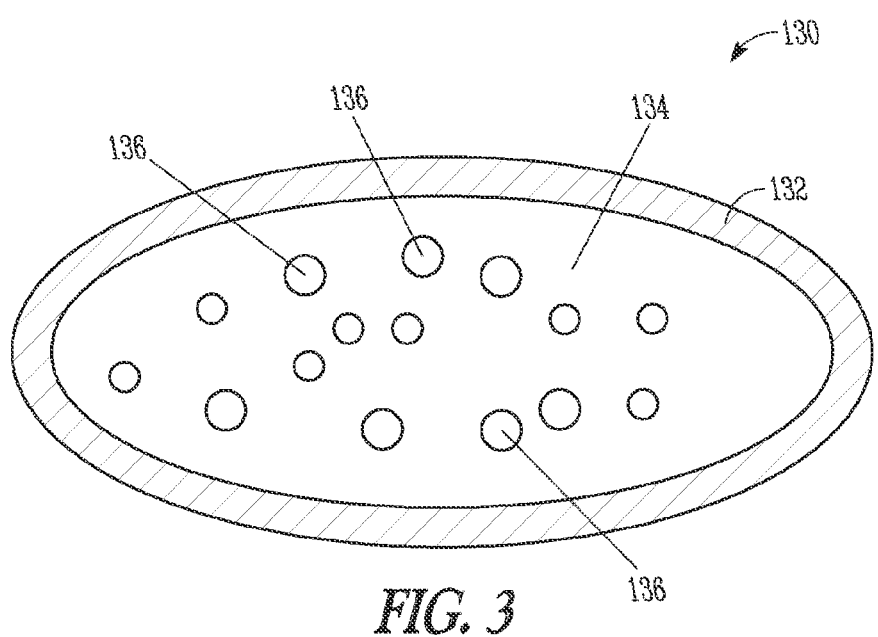
FIG. 3 is a sectional view of a tissue marker according to yet another embodiment.

FIG. 3 is a sectional view of another example tissue marker 130 according to another embodiment. The tissue marker 130 incorporates an outer capsule 132 formed from a nonbiodegradable radiopaque solid material, such as silicone. The capsule 132 is generally spheroid in shape and is preferably sized for insertion via a biopsy cannula. The capsule 132 defines an internal chamber 134.

One or more contrast agents 136 are introduced into the chamber 134, for example, by injecting the contrast agents 136 into the chamber 134. The visual representation of the contrast agents 136 in FIG. 3 is intended only to distinguish the contrast agents 136 from the chamber 134 in which they are disposed. According to various embodiments, the contrast agents 136 can be implemented as a gas, gel, or liquid, or as a combination of gases, gels, and/or liquids. Each of these materials can be selected independently to customize the appearance of the marker 130 in different imaging modalities and under different conditions, e.g., with or without contrast, and in various tissue types. For instance, if the marker 130 is to be visible in magnetic resonance (MR) and computed tomographic (CT) imaging modalities, the chamber 134 may contain a mixture of a gadolinium-DTPA MR contrast agent, such as MAGNEVIST® MR contrast agent, and an iodinated CT contrast agent, such as OMNIPAQUE™ CT contrast agent. The volume of contrast agent 136 in the chamber 134 may be maximized to promote visibility. Visibility is also promoted by matching the magnetic susceptibility of the contrast agent 136 and the magnetic susceptibility of the capsule 132. If it is further desired that the marker 130 be visible in an ultrasound imaging modality, the chamber 134 may also contain an air bubble. After the mixture is injected in the chamber 134, the capsule 132 is sealed.

In some embodiments, the capsule 132 itself, rather than multiple contrast agents 136, may provide visibility in certain imaging modalities. For example, the capsule 132 may be made of a radiopaque polymer that provides contrast in X-ray imaging modalities. As another example, a difference in acoustic impedance between the capsule 132 and the material in the chamber 134 will cause the marker 130 to reflect ultrasound waves, thereby promoting visibility in an ultrasound imaging modality. Further, if the magnetic susceptibility of the capsule 132 is similar to that of the material in the chamber 134 and to that of the surrounding tissue, visibility in MR imaging modalities will be improved due to reduction of $T_2$ darkening.

The markers 100, 120, and 130 illustrated in FIGS. 1-3 can be used for imaging a location within a patient's body. One or more markers are implanted near the location via, for example, a biopsy cannula. The markers can be implanted using any of a variety of conventional techniques, including, but not limited to, non-invasive medical procedures, biopsy procedures, injection, and conventional surgical procedures. In addition, the markers can be guided to a desired anatomical site during implantation using one or more imaging modalities in which the markers are detectable. For example, implantation can be guided using MRI, CT, or ultrasound modalities.

An image of the location is then generated in an MRI modality. In addition, another image of the location can be generated in another imaging modality, such as a CT X-ray imaging modality. Other imaging modalities may be employed, such as ultrasound, X-ray, fluoroscopy, electrical impedance tomography, magnetic source imaging (MSI), magnetic resonance spectroscopy (MRS), magnetic resonance mammography (MRM), magnetic resonance angiography (MRA), magnetoelectro-encephalography (MEG), laser optical imaging, electric potential tomography (EPT), brain electrical activity mapping (BEAM), arterial contrast injection angiography, digital subtraction angiography, positron emission tomography (PET), and single photon emission computed tomography (SPECT).

If multiple imaging modalities are employed, positional information for the area of the body that was imaged can be determined as a function of the images thus generated. For example, the images can be registered so as to align the coordinate systems of the images. In this way, any point in the imaged area of the body is made to correspond to identical addresses in each image. This registration process involves the use of rigid body transformation techniques, which in three-dimensional images requires knowledge of at least three points in each image. The markers described above may serve as fiducial markers to mark these points in the images. Accordingly, the fiducial markers can be used to correlate the spaces in each image, both with respect to physical space and with respect to the other images. In addition, the fiducial markers provide a constant frame of reference that is visible in each imaging modality to facilitate registration.

As demonstrated by the foregoing discussion, various embodiments may provide certain advantages, particularly in the context of imaging heterogeneous breast tissue. For instance, the use of a mixture of an MR contrast agent and a CT contrast agent may promote visibility in multiple imaging modalities, thus facilitating registering images obtained by multimodal imaging procedures. A contrast agent selected to produce an increase in signal intensity in an MR imaging modality may produce good visualization characteristics without also producing an excessive artifact and without interfering with MR spectroscopy. By producing an increase in signal intensity in MR imaging, the implantable tissue markers disclosed herein may be easier to see than conventional markers.

Because the contrast agents are sealed within the tube or capsule, they are at least substantially permanent and are not absorbed by the patient's body. Thus, multimodal imaging using the markers disclosed herein also allows a clinician to monitor an anatomical site over a period of time using images from multiple modalities, if desired. If the anatomical site in question requires treatment, the markers can be used to determine the precise location of the anatomical site and thus guide therapy. For example, markers can be implanted at a lesion site prior to removing the lesion to guide the procedure. After the lesion is removed, the markers can be used to monitor the site over time.

It will be understood by those who practice the embodiments described herein and those skilled in the art that various modifications and improvements may be made without departing from the spirit and scope of the disclosed embodiments. For example, the markers disclosed herein may incorporate therapeutic agents, such as radioactive agents, anti-inflammatory agents, anti-microbial agents, hemostatic agents, biocompatible adhesives, proteins, stem cells, or other material. Such agents may be applied to an external surface of the markers or disposed within the internal chambers. Accordingly, the scope of protection afforded is to be determined solely by the claims and by the breadth of interpretation allowed by law.

What is claimed is:

1. An apparatus comprising:
a permanently implantable radiographic marker including:
    a fully implantable, biocompatible container formed from a nonbiodegradable solid material and defining an internal chamber; and
    a contrast agent sealed within the internal chamber, the contrast agent including a liquid material configured to produce a change in signal intensity in a magnetic resonance (MR) imaging modality with the marker fully implanted in a human or animal subject, wherein the solid material of the container includes a first magnetic susceptibility and the liquid material of the contrast agent includes a second magnetic susceptibility, wherein the solid material and the liquid material are configured such that the first and second magnetic susceptibilities are matched so that the first magnetic susceptibility is substantially equivalent to the second magnetic susceptibility, wherein the permanently implantable radiographic marker is sized and shaped to fit within a lumen of a cannula configured to deliver the permanently implantable radiographic marker to a fully implanted location within the human or animal subject.

2. The apparatus of claim 1, wherein the contrast agent comprises at least another material selected from the group consisting of gas materials, liquid materials, and gel materials.

3. The apparatus of claim 1, wherein the container is generally spherical or spheroid in shape.

4. The apparatus of claim 1, further comprising a therapeutic agent.

5. The apparatus of claim 1, wherein the solid material forming the container is configured to produce a signal in another imaging modality.

6. The apparatus of claim 1, wherein the first magnetic susceptibility of the solid material of the container is substantially equivalent to a magnetic susceptibility of surrounding tissue.

7. The apparatus of claim 1, wherein the second magnetic susceptibility of the liquid material of the contrast agent is substantially equivalent to a magnetic susceptibility of surrounding tissue.

8. The apparatus of claim 1, wherein the permanently implantable radiographic marker, as a whole, includes an overall magnetic susceptibility substantially equivalent to a magnetic susceptibility of surrounding tissue.

9. The apparatus of claim 1, wherein the liquid material of the contrast agent is configured to produce an increased signal intensity.

10. The apparatus of claim 9, wherein the liquid material of the contrast agent is configured to produce the increased signal intensity in a T1-weighted MR image.

11. The apparatus of claim 1, wherein the container comprises a tube defining first and second end portions, and wherein the first and second end portions are at least substantially sealed.

12. The apparatus of claim 11, wherein the tube is formed from a solid material selected from the group consisting of glass materials, polymer materials, silicone, and carbon fiber.

13. The apparatus of claim 1, wherein the solid material forming the container is configured to produce a signal in another imaging modality in conjunction with the contrast agent sealed within the internal chamber.

14. The apparatus of claim 13, wherein the solid material forming the container and the contrast agent sealed within the internal chamber have different acoustic impedance characteristics.

15. The apparatus of claim 1, wherein the contrast agent includes a gas bubble.

16. The apparatus of claim 15, wherein the contrast agent, including the liquid material and the gas bubble, includes a magnetic susceptibility similar to a magnetic susceptibility of surrounding tissue.

17. The apparatus of claim 1, wherein the contrast agent comprises a mixture of a first contrast agent selected to produce the change in signal intensity in the MR imaging modality and a second contrast agent selected to produce a signal in another imaging modality.

18. The apparatus of claim 17, wherein the other imaging modality is one of an ultrasound imaging modality, an X-ray imaging modality, a fluoroscopy imaging modality, an electrical impedance tomographic imaging modality, a magnetic source imaging (MSI) modality, an magnetic resonance spectroscopic (MRS) modality, a magnetic resonance mammographic (MRM) modality, a magnetic resonance angiographic (MRA) modality, a magnetoelectroencephalographic (MEG) modality, a laser optical imaging modality, an electric potential tomographic (EPT) modality, a brain electrical activity mapping (BEAM) modality, an arterial contrast injection angiographic modality, a digital subtraction angiographic modality, a positron emission tomographic (PET) modality, and a single photon emission computed tomographic (SPECT) modality.

19. The apparatus of claim 17, wherein the first contrast agent comprises a paramagnetic material.

20. The apparatus of claim 19, wherein the first contrast agent comprises gadolinium.

21. The apparatus of claim 17, wherein the other imaging modality is a computed tomographic (CT) X-ray imaging modality.

22. The apparatus of claim 21, wherein the second contrast agent comprises iodine.

23. An apparatus comprising:
a permanently implantable fiducial marker including:
a fully implantable, biocompatible container formed from a nonbiodegradable solid material and defining an internal chamber;
a first contrast agent sealed within the internal chamber, the first contrast agent configured to produce an increase in signal intensity in a magnetic resonance (MR) imaging modality with the marker fully implanted in a human or animal subject; and
a second contrast agent sealed within the internal chamber, the second contrast agent configured to produce a signal in another imaging modality, wherein at least one of the first contrast agent or the second contrast agent includes a liquid material, and wherein the solid material of the container includes a solid material magnetic susceptibility and the liquid material of at least one of the first contrast agent or the second contrast agent includes a liquid material magnetic susceptibility, wherein the solid material and the liquid material are configured such that the solid material magnetic susceptibility and the liquid material magnetic susceptibility are matched so that the solid material magnetic susceptibility is substantially equivalent to the liquid material magnetic susceptibility, wherein the permanently implantable fiducial marker is sized and shaped to fit within a lumen of a cannula configured to deliver the permanently implantable fiducial marker to a fully implanted location within the human or animal subject.

24. The apparatus of claim 23, wherein the first and second contrast agents form a mixture.

25. The apparatus of claim 23, wherein the other imaging modality is one of an ultrasound imaging modality, an X-ray imaging modality, a fluoroscopy imaging modality, an electrical impedance tomographic imaging modality, a magnetic source imaging (MSI) modality, an magnetic resonance spectroscopic (MRS) modality, a magnetic resonance mammographic (MRM) modality, a magnetic resonance angiographic (MRA) modality, a magnetoelectroencephalographic (MEG) modality, a laser optical imaging modality, an electric potential tomographic (EPT) modality, a brain electrical activity mapping (BEAM) modality, an arterial contrast injection angiographic modality, a digital subtraction angiographic modality, a positron emission tomographic (PET) modality, and a single photon emission computed tomographic (SPECT) modality.

26. The apparatus of claim 23, wherein the first and second contrast agents each comprise at least one material selected from the group consisting of gas materials, liquid materials, and gel materials.

27. The apparatus of claim 23, wherein the container is generally spherical or spheroid in shape.

28. The apparatus of claim 23, further comprising a therapeutic agent.

29. The apparatus of claim 23, wherein the solid material magnetic susceptibility of the container is substantially equivalent to a magnetic susceptibility of surrounding tissue.

30. The apparatus of claim 23, wherein the liquid material magnetic susceptibility of at least one of the first contrast agent or the second contrast agent is substantially equivalent to a magnetic susceptibility of surrounding tissue.

31. The apparatus of claim 23, wherein the permanently implantable fiducial marker, as a whole, includes an overall magnetic susceptibility substantially equivalent to a magnetic susceptibility of surrounding tissue.

32. The apparatus of claim 23, wherein the first contrast agent comprises a paramagnetic material.

33. The apparatus of claim 32, wherein the first contrast agent comprises gadolinium.

34. The apparatus of claim 23, wherein the other imaging modality is a computed tomographic (CT) X-ray imaging modality.

35. The apparatus of claim 34, wherein the second contrast agent comprises iodine.

36. The apparatus of claim 23, wherein the container comprises a tube defining first and second end portions, and wherein the first and second end portions are at least substantially sealed using a biocompatible adhesive.

37. The apparatus of claim 36, wherein the tube is formed from a nonbiodegradable solid material selected from the group consisting of glass materials, polymer materials, silicone, and carbon fiber.

38. The apparatus of claim 23, wherein at least one of the first contrast agent or the second contrast agent includes a gas bubble.

39. The apparatus of claim 38, wherein at least one of the first contrast agent or the second contrast agent, including the liquid material and the gas bubble, includes a magnetic susceptibility substantially equivalent to a magnetic susceptibility of surrounding tissue.

40. The apparatus of claim 23, wherein the liquid material of at least one of the first contrast agent or the second contrast agent is configured to produce an increased signal intensity.

41. The apparatus of claim 40, wherein the liquid material of the at least one of the first contrast agent or the second contrast agent is configured to produce the increased signal intensity in a T1-weighted MR image.

42. A method of identifying a location within a body of a patient, the method comprising:
    fully implanting a marker proximate the location using a cannula, the marker comprising a fully implantable, biocompatible container formed from a solid nonbiodegradable material and defining an internal chamber, the marker further comprising a contrast agent sealed within the internal chamber, the contrast agent including a liquid material configured to produce an increase in signal intensity in a magnetic resonance (MR) imaging modality with the marker fully implanted in a human or animal subject, wherein the solid material of the container includes a first magnetic susceptibility and the liquid material of the contrast agent includes a second magnetic susceptibility, wherein the solid material and the liquid material are configured such that the first and second magnetic susceptibilities are matched so that the first magnetic susceptibility is substantially equivalent to the second magnetic susceptibility, wherein the marker is configured to fit within a lumen of the cannula; and
    generating a first image of the location in the magnetic resonance (MR) imaging modality.

43. The method of claim 42, wherein the contrast agent comprises at least another material selected from the group consisting of gas materials, liquid materials, and gel materials.

44. The method of claim 42, wherein the container is generally spherical or spheroid in shape.

45. The method of claim 42, wherein the solid material forming the container is configured to produce a signal in another imaging modality.

46. The method of claim 42, wherein the first magnetic susceptibility of the solid material of the container is substantially equivalent to a magnetic susceptibility of surrounding tissue.

47. The method of claim 42, wherein the second magnetic susceptibility of the liquid material of the contrast agent is substantially equivalent to a magnetic susceptibility of surrounding tissue.

48. The method of claim 42, wherein the permanently implantable radiographic marker, as a whole includes an overall magnetic susceptibility substantially equivalent to a magnetic susceptibility of surrounding tissue.

49. The method of claim 42, wherein the container comprises a tube defining first and second end portions that are at least substantially sealed using a biocompatible adhesive.

50. The method of claim 49, wherein the tube is formed from a solid material selected from the group consisting of glass materials, polymer materials, silicone, and carbon fiber.

51. The method of claim 42, wherein the solid material forming the container is configured to produce a signal in another imaging modality in conjunction with the contrast agent sealed within the internal chamber.

52. The method of claim 51, wherein the solid material forming the container and the contrast agent sealed within the internal chamber have different acoustic impedance characteristics.

53. The method of claim 42, wherein the contrast agent includes a gas bubble.

54. The method of claim 53, wherein the contrast agent, including the liquid material and the gas bubble, includes a magnetic susceptibility substantially equivalent to a magnetic susceptibility of surrounding tissue.

55. The method of claim 42, wherein the liquid material of the contrast agent is configured to produce an increased signal intensity.

56. The method of claim 55, wherein the liquid material of the contrast agent is configured to produce the increased signal intensity in a T1-weighted MR image.

57. The method of claim 42, further comprising generating a second image of the location in another imaging modality, wherein the contrast agent comprises a mixture of a first contrast agent configured to produce the increase in signal intensity in the MR imaging modality and a second contrast agent configured to produce a signal in the other imaging modality.

58. The method of claim 57, wherein the other imaging modality is one of an ultrasound imaging modality, an X-ray imaging modality, a fluoroscopy imaging modality, an electrical impedance tomographic imaging modality, a magnetic source imaging (MSI) modality, an magnetic resonance spectroscopic (MRS) modality, a magnetic resonance mammographic (MRM) modality, a magnetic resonance angiographic (MRA) modality, a magnetoelectroencephalographic (MEG) modality, a laser optical imaging modality, an electric potential tomographic (EPT) modality, a brain electrical activity mapping (BEAM) modality, an arterial contrast injection angiographic modality, a digital subtraction angiographic modality, a positron emission tomographic (PET) modality, and a single photon emission computed tomographic (SPECT) modality.

59. The method of claim 57, wherein the first contrast agent comprises a paramagnetic material.

60. The method of claim 59, wherein the first contrast agent comprises gadolinium.

61. The method of claim 57, wherein the other imaging modality is a computed tomographic (CT) X-ray imaging modality.

62. The method of claim 61, wherein the second contrast agent comprises iodine.

* * * * *